United States Patent [19]

Sakuma et al.

[11] Patent Number: 5,468,489
[45] Date of Patent: Nov. 21, 1995

[54] DENTIFRICE CONTAINING ANTIBACTERIAL MATERIAL

[75] Inventors: Shuji Sakuma; Kiminori Atsumi, both of Tokyo, Japan

[73] Assignee: Sangi Co., Ltd., Tokyo, Japan

[21] Appl. No.: 262,378

[22] Filed: Jun. 20, 1994

Related U.S. Application Data

[63] Continuation of Ser. No. 986,451, Dec. 7, 1992, abandoned, which is a continuation-in-part of Ser. No. 870,906, Apr. 20, 1992, abandoned.

[30] Foreign Application Priority Data

Oct. 29, 1991 [JP] Japan .................. 3-282636

[51] Int. Cl.$^6$ .................................................. A61K 7/16
[52] U.S. Cl. ........................ 424/49; 424/57; 424/618; 424/630; 424/641
[58] Field of Search .................. 424/49, 57, 618, 424/630, 641

[56] References Cited

U.S. PATENT DOCUMENTS

| | | | |
|---|---|---|---|
| 3,989,814 | 11/1976 | Cordon et al. | 424/57 |
| 4,048,300 | 9/1977 | Tomlinson et al. | 424/52 |
| 4,108,980 | 8/1978 | Duff | 424/52 |
| 4,139,599 | 2/1979 | Tomlinson et al. | 423/308 |
| 4,327,079 | 4/1982 | Aoki | 424/57 |
| 4,342,741 | 8/1982 | Aoki | 424/57 |
| 4,634,589 | 1/1987 | Scheller | 424/49 |
| 4,710,372 | 12/1987 | Scheller | 424/49 |
| 5,009,898 | 4/1991 | Sakuma et al. | 424/618 |
| 5,009,898 | 4/1991 | Sakuma et al. | 424/57 |
| 5,151,122 | 9/1992 | Atsumi et al. | 106/35 |
| 5,266,534 | 11/1993 | Atsumi et al. | 501/1 |
| 5,324,525 | 6/1994 | Sakuma et al. | 424/602 |

FOREIGN PATENT DOCUMENTS

| | | | |
|---|---|---|---|
| 48922/79 | 11/1979 | Australia . | |
| 17460/88 | 12/1988 | Australia . | |
| 34808/89 | 11/1989 | Australia . | |
| 34809/89 | 11/1989 | Australia . | |
| 34810/89 | 11/1989 | Australia . | |
| 0428493 | 5/1991 | European Pat. Off. . | |
| 1-236008 | 9/1989 | Japan | 424/57 |
| 1-238508 | 9/1989 | Japan | 424/57 |
| 2-237639 | 9/1990 | Japan | 424/57 |
| 3-200702 | 9/1991 | Japan | 424/57 |
| 3-271209 | 12/1991 | Japan | 424/57 |
| 2224727 | 5/1990 | United Kingdom | 424/57 |
| 2236676 | 4/1991 | United Kingdom | 424/57 |
| 2238044 | 5/1991 | United Kingdom | 424/57 |

OTHER PUBLICATIONS

Atsumi et al C.A. 115:214931w (1991) of Brit. UK/GB2238044 22 May 1991.

Hangst et al and Eitenmuller et al CA. 112:25543y and 25544z (1990).

*Primary Examiner*—Ronald W. Griffin
*Attorney, Agent, or Firm*—Foley & Lardner

[57] ABSTRACT

A dentifrice (tooth paste) having an antibacterial effect to prevent production of carious tooth and generation of periodontal diseases such as alveolar blennorrhea. The dentifrice contains hydroxylapatite powder. The hydroxylapatite powder carries therein an antibacterial metal such as silver, copper and/or zinc. The antibacterial metal is adsorbed to and/or combined, under ion exchange, with the hydroxylapatite powder.

17 Claims, No Drawings

DENTIFRICE CONTAINING ANTIBACTERIAL MATERIAL

This application is a continuation of application Ser. No. 07/986,451, filed Dec. 7, 1992, now abandoned which is a continuation-in-part application of U.S. patent application Ser. No. 07/870,906, filed Apr. 20, 1992, now abandoned.

BACKGROUND OF THE INVENTION

1. Field of the Invention

This invention relates to improvements in a dentifrice (tooth paste or powder), and more particularly to the dentifrice having an antibacterial effect.

2. Description of the Prior Art

In general, a dentifrice (tooth paste or powder) includes abrasive powder, foaming agent, perfume and taste adjusting agents, lubricant, caking additive and medicative ingredients as main components. In recent years, a dentifrice provided with an antibacterial effect has been developed, in which organic substances such as parahydroxybenzoates, chlorhexidines, hinokitiol and protamine and inorganic substances such as salt are known and used as materials exhibiting an antibacterial effect.

However, such a dentifrice containing the antibacterial materials is problematic from view points of toxicity, stability and taste, owing to the character of the antibacterial materials. Particularly, almost all the conventional antibacterial materials are low in heat-resistance and soluble in water, and therefore difficult to be thermally processed and not durable to use for a long period of time.

In this connection, it is known that metals such as silver, copper and zinc and salts thereof exhibit a high antibacterial effect. However, these metals or the salts cannot be safely used in a dentifrice (tooth paste) because metal ions of the metal tend to be readily released thereby causing a toxicity.

SUMMARY OF THE INVENTION

It is an object of the present invention to provide an improved dentifrice (tooth paste or powder) which can overcome the drawbacks encountered in conventional dentifrices.

Another object of the present invention is to provide an improved dentifrice (tooth paste or powder) which is high in safety and stability, while maintaining a high antibacterial effect.

A further object of the present invention is to provide an improved dentifrice (tooth paste or powder) in which an antibacterial material is stably and firmly carded or supported by a carrier as a component of the dentifrice.

An aspect of the dentifrice (tooth paste or powder) of the present invention comprises a calcium compound, and an antibacterial metal carded by the calcium compound. Another aspect of the dentifrice of the present invention comprises a phosphate containing calcium, and an antibacterial metal carried in a metallic state by the calcium containing phosphate. Accordingly, the dentifrice exhibits a high antibacterial effect. The antibacterial metal carded by the calcium compound is highly stable, and therefore the toxicity due to the ion form of the metal is prevented while contributing to a medical treatment of teeth and further providing the dentifrice with a good preservability for a long period of time. Thus, the dentifrice of the present invention is highly effective for preventing occurrence of carious tooth and periodontal diseases such as alveolar blennorrhea.

DETAILED DESCRIPTION OF THE INVENTION

A dentifrice (tooth paste: or powder) according to the present invention is comprised of a calcium compound, and an antibacterial metal carried by the calcium compound. More specifically, the dentifrice according to the present invention is comprised of a phosphate containing calcium (such as hydroxylapatite, tricalcium phosphate and calcium diphosphate), and the antibacterial metal carded in its metallic state by the calcium containing phosphate.

Examples of the calcium compound are calcium hydrogenphosphate $CaHPO_4 \cdot 0-2H_2O$, tricalcium phosphate $Ca_3(PO_4)_2$, calcium diphosphate $Ca_2P_2O_7$, calcium carbonate $CaCO_3$ and the like. Examples of the antibacterial metal are silver (Ag), zinc (Zn), copper (Cu) and the like. The antibacterial metal(s) are carried by or combined to the calcium compound under an ion exchange and/or adsorption, thereby forming an antibacterial calcium compound(s). The antibacterial calcium compound(s) is mixed in the dentifrice (tooth paste or powder). The use of the antibacterial metal adds the functions of preventing generation of carious tooth and periodontal diseases such as alveolar blennorrhea, to the dentifrice.

A method of production of an antibacterial calcium hydrogenphosphate will be discussed. First, metallic salt(s) such as silver nitrate or silver sulfate is added to an aqueous suspension of calcium hydrogenphosphate under agitation to promote the reaction between the metallic salt(s) and the calcium hydrogenphosphate, thereby forming a reaction product. Thereafter, the reaction product is rinsed, dehydrated and dried thereby to obtain the antibacterial calcium hydrogenphosphate. Besides, the antibacterial calcium hydrogenphosphate is obtained by firing the above-mentioned dehydrated and dried reaction product at a temperature of 800° C. or higher, or by reducing the above-mentioned dehydrated and dried reaction product with hydrogen, in which the antibacterial metal(s) are carried in a metallic state (not in an ionic or salt state) on the calcium compound. In the process of the heating or the reduction with hydrogen, the antibacterial metal will be converted from its ionic state to its metallic state. It will be understood that antibacterial hydroxylapatite, antibacterial tricalcium phosphate, antibacterial calcium diphosphate, antibacterial calcium carbonate and the like can be obtained by the same production method as that of the antibacterial calcium hydrogenphosphate and the like in which the antibacterial metal is carried in its metallic state by the calcium hydrogenphosphate.

For example, an antibacterial phosphate containing calcium (such as hydroxylapatite, tricalcium phosphate and calcium diphosphate) is prepared by virtue of using a firing step as follows:

Hydroxylapatite in an amount of 1.0 kg is added to 10 liters of water together with 32 g of silver nitrate and 69 g of zinc nitrate, and then the whole was stirred to make a reaction. The solids are separated off to form a cake, then the cake is rinsed thoroughly with distilled water and dried. The washed cake is heated or fired at 1200° C. and powdered to provide the antibacterial hydroxylapatite carrying about 2% by weight of silver in a metallic state and 1.5% by weight of zinc in a metallic state.

Tricalcium phosphate in an amount of 1.0 kg of tricalcium phosphate is added to 10 liters of distilled water together with 30 g of silver nitrate and 45 g of zinc nitrate, and the whole is stirred to make a reaction. The solids are separated off to form a cake, and then the cake is rinsed thoroughly with distilled water and dried. The dried cake is heated or fired at 1100° C. and powdered to provide the antibacterial tricalcium phosphate carrying about 0.5% by weight of silver in a metallic state and about 1% by weight of zinc in a metallic state.

Otherwise, the antibacterial phosphate containing calcium carrying an antibacterial metal such as silver is prepared by virtue of using a reduction step as follows:

Metallic salt(s) such as silver nitrate and/or silver sulfate is added to an aqueous suspension of the calcium containing phosphate under agitation to promote the reaction between the metallic salt(s) and the phosphate, thereby forming a reaction product or solid in which metallic ion and/or the metallic salt is supported on the phosphate. Thereafter, the reaction product is rinsed, dehydrated and dried. The dried reaction product is put in a reaction tube and heated at a temperature of 350° C. or higher in the stream of hydrogen so as to reduce the metallic ion and/or metallic salt, thereby obtaining the antibacterial phosphate carrying the antibacterial metal in a metallic state.

An antibacterial calcium hydrogenphosphate (carrying or containing 0.1 wt % of silver), an antibacterial tricalcium phosphate (carrying or containing 2 wt % of silver and 3 wt % of zinc), an antibacterial calcium diphosphate (containing or carrying 1 wt % of silver and 2 wt % of zinc), and an antibacterial calcium carbonate (containing or carrying 0.001 wt % of silver) will be used in Experiment 1 set forth below. It will be appreciated that these antibacterial materials were prepared by methods similar to those mentioned above for the antibacterial phosphate containing calcium, so that the antibacterial metal(s) is carried in a metallic state on the calcium compound in the antibacterial materials to be used in Experiment 1.

The amount of the antibacterial metal carried by the calcium compound is suitably selected according to the kind of the metallic salt to be used, the concentration and the temperature of the aqueous suspension of the calcium compound. The amount of the antibacterial metallic salt is preferably not more than 30% by weight, and more preferably 5 to 0.0001% by weight relative to the amount of the calcium compound such as calcium phosphate and calcium carbonate.

The thus obtained antibacterial calcium compound exhibits a sufficient antibacterial effect even upon addition of a small amount thereof to the dentifrice, maintaining the antibacterial effect for a long period of time. Additionally, the antibacterial calcium compound can be safely used since the amount of released metal to water is extremely small, i.e., less than several ppb.

EXPERIMENT 1

The dentifrice of the pre, sent invention will be discussed further in detail with reference to experiments for Examples and Comparative Example.

[Preparation of Specimen Tooth Paste and Powder]

in this experiment, first specimen tooth pastes having compositions of Examples 1 to 4 and of Comparative Example 1 were prepared by mixing components listed below in each Example. It will be understood that the antibacterial calcium compound carrying the antibacterial metal(s) to be used in Examples 1 to 4 were previously prepared as discussed above.

EXAMPLE 1 (Tooth Paste)

| | |
|---|---|
| Antibacterial calcium hydrogenphosphate (silver 0.1 wt % contained) | 41.0 wt % |
| Glycerine | 20.0 wt % |
| Carageenan | 1.1 wt % |
| Sodium lauryl sulfate | 1.5 wt % |
| Saccharin | 1.0 wt % |
| Perfume | 1.0 wt % |
| Butyl para-hydroxybenzoate | 0.005 wt % |
| Water | balance |

EXAMPLE 2 (Tooth Paste)

| | |
|---|---|
| Antibacterial tricalcium phosphate (silver 2 wt % and zinc 3 wt % contained) | 3.0 wt % |
| Aluminum hydroxide | 37.0 wt % |
| Carboxymethyl cellulose | 1.3 wt % |
| Sorbitol | 19.0 wt % |
| Propylene glycol | 2.0 wt % |
| Sodium lauryl sulfate | 1.0 wt % |
| Sodium saccharin | 1.0 wt % |
| Perfume | 1.1 wt % |
| Butyl para-hydroxybenzoate | 0.005 wt % |
| Water | balance |

EXAMPLE 3 (Tooth Paste)

| | |
|---|---|
| Antibacterial calcium diphosphate (silver 1 wt % and Zinc 2 wt % contained) | 42.0 wt % |
| Calcium lauryl sulfate | 1.2 wt % |
| Sodium lauroyl sarcosinate | 0.2 wt % |
| Glycerine | 20.0 wt % |
| Carageenan | 1.1 wt % |
| Ester of saccharose fatty acid | 2.0 wt % |
| Perfume | 1.2 wt % |
| Water | balance |

EXAMPLE 4 (Tooth Powder)

| | |
|---|---|
| Antibacterial calcium carbonate (silver 0.001 wt % contained) | 75.0 wt % |
| Grycerine | 10.0 wt % |
| Perfume | 1.0 wt % |
| Butyl para-hydroxylbenzoate | 0.005 wt % |
| Sodium lauryl sulfate | 1.3 wt % |
| Saccharin | 0.1 wt % |
| Water | balance |

COMPARATIVE EXAMPLE 1 (Tooth Paste)

| | |
|---|---|
| Calcium hydrogenphosphate | 41.0 wt % |
| Glycerine | 20.0 wt % |
| Carageenan | 1.1 wt % |
| Sodium lauryl sulfate | 1.5 wt % |
| Saccharin | 1.0 wt % |
| Perfume | 1.0 wt % |
| Butyl para-hydroxybenzoate | 0.005 wt % |
| Water | balance |

[Antibacterial Test]

1 gram of each specimen tooth paste prepared in Examples 1 to 4 and Comparative Examples 1 and 2 was added to 10 ml of a liquid containing each of bacillus (streptococcus mutans type G and streptococcus sanguis as bacilluses or causatives for carious tooth, and actinobacillus actinomycetemcomitans Y4 and bacteroides gingivalis as bacillus or causatives for periodontal diseases) in a flask. The flask was shaken according to a so-called shake flask method in which the number of living bacillus was measured with lapse of time in order to evaluate an antibacterial. effect. The result of the antibacterial test is shown in Table 1.

TABLE 1

| Bacillus | Sample | Living bacillus (number/ml) | | |
|---|---|---|---|---|
| | | 0 hr. lapsed | 6 hrs. after | 12 hrs. after |
| Streptococcus mutans type G | Example 1 | $6.8 \times 10^5$ | <1 | <1 |
| | Example 2 | $6.8 \times 10^5$ | <1 | <1 |
| | Example 3 | $6.8 \times 10^5$ | <1 | <1 |
| | Example 4 | $6.8 \times 10^5$ | <1 | <1 |
| | Comparative Example 1 | $6.8 \times 10^5$ | $9.5 \times 10^4$ | $4.1 \times 10^5$ |
| Streptococcus sanguis | Example 1 | $4.0 \times 10^5$ | $8.2 \times 10^2$ | <1 |
| | Example 2 | $4.0 \times 10^5$ | <1 | <1 |
| | Example 3 | $4.0 \times 10^5$ | $3.3 \times 10$ | <1 |
| | Example 4 | $4.0 \times 10^5$ | $3.7 \times 10^2$ | $4.9 \times 10$ |
| | Comparative Example 1 | $4.0 \times 10^5$ | $5.7 \times 10^5$ | $6.4 \times 10^5$ |
| Actinobacillus actinomycetem-comitans Y4 | Example 1 | $3.7 \times 10^5$ | $2.4 \times 10$ | <1 |
| | Example 2 | $3.7 \times 10^5$ | <1 | <1 |
| | Example 3 | $3.7 \times 10^5$ | <1 | <1 |
| | Example 4 | $3.7 \times 10^5$ | $1.5 \times 10^2$ | <1 |
| | Comparative Example 1 | $3.7 \times 10^5$ | $2.9 \times 10^5$ | $2.2 \times 10^5$ |
| Bacteroides gingivalis | Example 1 | $6.5 \times 10^5$ | $1.8 \times 10^2$ | <1 |
| | Example 2 | $6.5 \times 10^5$ | $1.7 \times 10$ | <1 |
| | Example 3 | $6.5 \times 10^5$ | <1 | <1 |
| | Example 4 | $6.5 \times 10^5$ | $5.1 \times 10^3$ | $2.6 \times 10$ |
| | Comparative Example 1 | $6.5 \times 10^5$ | $8.4 \times 10^5$ | $1.5 \times 10^5$ |

As can be appreciated from Table 1, the specimen tooth pastes of Examples (according to the present invention) are considerably high in antibacterial effect to the bacillus for carious tooth and periodontal diseases such as alveolar blennorrhea, as compared with that of Comparative Example (a conventional tooth paste). Additionally, a released metal content test for the specimen tooth pastes were conducted, which revealed that no releasing of the antibacterial metal was recognized.

While only silver and zinc have been described as being used as the antibacterial metal in Examples, it will be appreciated that they may be replaced with other antibacterial metals.

The above-mentioned examples of the calcium compound includes apatite. In case of using apatite as the calcium compound of the present invention, the antibacterial metal such as silver (Ag), copper (Cu) and/or zinc (Zn) is carried by or combined with the apatite under ion exchange and/or adsorption thereby to form an antibacterial apatite. The thus formed antibacterial apatite takes the form of $Ca_{10-x}M_x(PO_4)_5(OH_2)$, $Ca_{10}(M \cdot PO_4)_5(OH)_2$ or the like, in which M is the antibacterial metal, and x is an integer or decimal larger than 0. The antibacterial apatite is mixed in the dentifrice (tooth paste). The antibacterial apatite is stable and heat-resistive, and good in mixability with the tooth paste since the apatite is in the state of powder.

The antibacterial apatite can be easily produced under coexistence of the metallic salt of the antibacterial metal(s) during synthesis of the apatite, or by reacting the metallic salt with the apatite. More specifically, according to the former method, a phosphoric acid aqueous solution is dropped to an aqueous solution containing calcium hydroxide and the metallic salt(s) of silver, copper, zinc and/or the like under stirring thereby synthesizing the antibacterial apatite. According to the latter method, fine powder of the apatite obtained under the conventional method is suspended in distilled water to form a suspension. To the suspension, a water-soluble metallic salt(s) of the antibacterial metal(s) is added and then stirred to promote the reaction between the apatite and the antibacterial metal(s) thereby to form a product. Thereafter, the product is rinsed, dried and pulverized thus obtaining the antibacterial apatite.

In the above production processes, there is the possibility that calcium salt remains in the resultant antibacterial apatite, the calcium salt being formed during the reaction process in which acidic roots, the metallic salts and metallic ions are replaced with calcium ions. Accordingly, it is preferable that the resultant antibacterial apatite is sufficiently rinsed with water in order to completely remove these foreign matters.

The amount of the antibacterial metal carried by the apatite is suitably selected according to the kind of the antibacterial metal to be used, and the concentration and the temperature of the aqueous solution containing the apatite or raw materials of the apatite. The amount of the antibacterial metal is preferably not more than 30% by weight, more preferably 5 to 0.0001% by weight relative to the apatite.

The thus obtained antibacterial apatite exhibits a sufficient antibacterial effect even upon addition of a small amount thereof to the dentifrice, maintaining the antibacterial effect for a long period of time. Additionally, the antibacterial apatite can be safely used since the amount of released metal to water is very small, i.e., less than several ppb.

EXPERIMENT 2

The antibacterial apatite will be discussed further in detail with reference to experiments conducted to evaluate advantageous effects of the antibacterial apatite.

[Preparation of Specimen Tooth Paste]

Specimen tooth pastes having compositions of Examples 5 and 6 and Comparative Examples 2 and 3 were prepared. In Example 5, the antibacterial apatite was a hydroxylapatite carrying 2% by weight of silver and 3% by weight of zinc which were adsorbed to or combined (under ion exchange) with the apatite. The antibacterial hydroxylapatite obtained under the ion exchange seems to take the form of $Ca_{10-x-y} \cdot Zn_y \cdot Ag_x(PO_4)_6(OH)_2$, $Ca_{10-y} \cdot Zn_y(Ag \cdot PO_4)_6(OH)_2$ or the like, in which x and y are respectively integers or decimals larger than 0. In Example 6, the antibacterial apatite was a hydroxylapatite carrying 0.1% wt weight of silver which had been absorbed to and carried (under ion exchange) by the hydroxylapatite. The antibacterial hydroxylapatite obtained under the ion exchange seems to take the form of $Ca_{10-x} \cdot Ag_x(PO_4)_6(OH)_2$, $Ca_{10}(Ag \cdot PO_4)_6(OH)_2$ or the like.

EXAMPLE 5

| | |
|---|---|
| Antibacterial hydroxylapatite | 5.0 wt % |
| Calcium phosphate | 10.0 wt % |
| Calcium pyrophosphate | 20.0 wt % |
| Sodium salt CMC | 1.0 wt % |
| Sodium alginate | 0.1 wt % |

-continued

| | |
|---|---|
| Sorbitol | 10.0 wt % |
| Sodium lauryl sulfate | 1.5 wt % |
| Lauroyl sarcosine sodium | 0.5 wt % |
| Perfume | 0.5 wt % |
| Sodium saccharin | 0.1 wt % |
| Silicon nitride | 2.5 wt % |
| Citric acid | 2.0 wt % |
| Sodium phosphate | 1.0 wt % |
| Water | 35.0 wt % |

EXAMPLE 6

| | |
|---|---|
| Antibacterial hydroxylapatite | 50.0 wt % |
| Calcium phosphate | 25.0 wt % |
| Sodium salt CMC | 0.3 wt % |
| Carageenan | 1.2 wt % |
| Glycerine | 5.0 wt % |

REFERENCE EXAMPLE 1

| | |
|---|---|
| Antibacterial hydroxylapatite (powder) carrying 1% by weight of silver (Ag) and 0.3% by weight of copper (Cu) | 100 wt % |

COMPARATIVE EXAMPLE 2

| | |
|---|---|
| Hydroxylapatite | 5.0 wt % |
| Calcium phosphate | 10.0 wt % |
| Calcium pyrophosphate | 20.0 wt % |
| Sodium salt CMC | 1.0 wt % |
| Sodium alginate | 0.1 wt % |
| Sorbitol | 10.0 wt % |
| Sodium lauryl sulfate | 1.5 wt % |
| Lauroyl sarcosine sodium | 0.5 wt % |
| Perfume | 0.5 wt % |
| Sodium saccharin | 0.1 wt % |
| Silicon dioxide | 2.5 wt % |
| Citric acid | 2.0 wt % |
| Sodium phosphate | 1.0 wt % |
| Water | 35.0 wt % |

[Antibacterial Test (I)]

In case of Examples 5 and 6 and Comparative Example 2, 1 gram of each specimen tooth paste was sampled. In case of Reference Example 1, 0.001 gram of the powder of the antibacterial hydroxylapatite was sampled. Each of the thus sampled specimen tooth paste and the hydroxylapatite powder was added to 10 ml of a liquid containing each of bacillus (streptococcus mutans type G and streptococcus sanguis as bacillus or causatives for carious tooth, and actinobacillus actinomycetemcomitans Y4 and bacteroides gingivalis as bacillus or causatives for periodontal diseases) in a flask. The flask was shaken according to the shake flask method in which the number of living bacillus was measured with lapse of time in order to evaluate an antibacterial effect. The result of the antibacterial test is shown in Table 2.

TABLE 2

| | | Living bacillus (number/ml) | | |
|---|---|---|---|---|
| Bacillus | Sample | 0 hr. lapsed | 6 hrs. after | 12 hrs. after |
| Streptococcus mutans type G | Example 5 | $6.8 \times 10^6$ | <1 | <1 |
| | Example 6 | $6.8 \times 10^6$ | <1 | <1 |
| | Reference Example 1 | $6.8 \times 10^6$ | <1 | <1 |
| | Comparative Example 2 | $6.8 \times 10^6$ | $1.7 \times 10^5$ | $2.0 \times 10^5$ |
| Streptococcus sanguis | Example 5 | $4.0 \times 10^6$ | $7.5 \times 10^2$ | <1 |
| | Example 6 | $4.0 \times 10^6$ | $1.6 \times 10^3$ | <1 |
| | Reference Example 1 | $4.0 \times 10^6$ | $3.8 \times 10^3$ | <1 |
| | Comparative Example 2 | $4.0 \times 10^6$ | $3.7 \times 10^6$ | $4.5 \times 10^6$ |
| Actinobacillus actinomycetem- comitans Y4 | Example 5 | $3.7 \times 10^5$ | <1 | <1 |
| | Example 6 | $3.7 \times 10^5$ | $2.4 \times 10^2$ | <1 |
| | Reference Example 1 | $3.7 \times 10^5$ | $1.5 \times 10$ | <1 |
| | Comparative Example 2 | $3.7 \times 10^5$ | $3.5 \times 10^5$ | $4.6 \times 10^5$ |
| Bacteroides gingivalis | Example 5 | $6.5 \times 10^5$ | $5.4 \times 10$ | <1 |
| | Example 6 | $6.5 \times 10^5$ | $8.3 \times 10^2$ | <1 |
| | Reference Example 1 | $6.5 \times 10^5$ | $3.1 \times 10^3$ | <1 |
| | Comparative Example 2 | $6.5 \times 10^5$ | $6.7 \times 10^5$ | $5.2 \times 10^5$ |

As can be appreciated from the test result of Table 2, the composition of the tooth pastes of the above Examples exhibits a sufficient antibacterial effect against the bacillus which causes carious tooth and for periodontal diseases. Additionally, as a result of further tests conducted in which the content or blended ratio of the antibacterial hydroxylapatite was changed in the above specimen tooth paste of Examples 5 and 6, it was revealed that a sufficient antibacterial effect was exhibited if only 0.01% by weight of the antibacterial hydroxylapatite was added to the tooth paste.

[Antibacterial Test (II)]

In this test, the antibacterial effect of only the antibacterial hydroxylapatite was measured. The test was conducted on the antibacterial hydroxylapatites used in Examples 5 and 6 as follows: First, binder was added to and mixed with the antibacterial hydroxylapatite to form a mixture. The mixture was subjected to a compression-molding and then degreased at 500° C. thereby to obtain a pellet (formed of the antibacterial hydroxylapatite 100%) having a diameter of 3 cm. Thereafter, *escherichia coli* (*E. coli*) was adhered to the pellet, upon which the change of the number of living bacillus with the lapse of time was observed. The test result is shown in Table 3.

TABLE 3

| Bacillus | Lapsed time and number of living bacillus | |
|---|---|---|
| Escherichia coli | 0 hr. $6.8 \times 10^4$ | 48 hrs. 10 or less |

[Released Metal Content Test]

In this test, the released amount of the carded antibacterial metal was measured for a first sample of the hydroxylapatite carrying 5% by weight of silver (Ag) as the antibacterial metal, and for a second sample of the hydroxylapatite carrying 5% by weight of zinc (Zn) as the antibacterial metal. The test was conducted as follows: First, 1 gram of each of the first and second sample hydroxylapatites was added to 100 cc of distilled water and stirred for a long period of time. Then, measurement was made on the concentration of the metal released from the hydroxylapatite to the aqueous solution. As a result, in case of the first sample, the concentration of the released metal was 0.01 ppm or less. In case of the second sample, the concentration was 0.2 ppm or less. Accordingly, it was confirmed that the antibacterial metal carded by the hydroxylapatite was not released at all to water. Additionally, it was also confirmed that no change occurred in the concentration of the released metal even upon lapse of time. This revealed that the antibacterial hydroxylapatite was highly stable as a molecule, which seemed to be caused because of the fact that the antibacterial metal was indeed firmly combined with or taken up into the fine pores of the molecule structure of the hydroxylapatite.

The antibacterial hydroxylapatite has functions to separate protein and to remove dental plaque as a source for producing carious tooth, and therefore has a further effect to preventing occurrence of the carious tooth in addition to the above-discussed antibacterial effect. Moreover, the antibacterial hydroxylapatite functions to be filled in fine grooves or depressions on the surface of teeth thereby accomplishing the restoration of the teeth.

As appreciated from the above, the antibacterial hydroxylapatite is stable in molecular structure and therefore is prevented from exhibition of toxicity due to the antibacterial metal, maintaining a good preservability for a long period of time. Thus, the dentifrice (tooth paste) containing the antibacterial hydroxylapatite, according to the present invention is very effective for preventing occurrence of carious tooth and periodontal diseases, suppressing occurrence of hyperesthesia due to the carious tooth and the periodontal diseases and other oral disorders in general.

What is claimed is:

1. A dentifrice comprising:

a phosphate containing calcium; and an antibacterial metal carded in a metallic state by said calcium containing phosphate, said antibacterial metal being at least one metal selected from the group consisting of silver, copper and zinc.

2. A dentifrice comprising:

a phosphate containing calcium; and an antibacterial metal carried in a metallic state by said calcium containing phosphate, said antibacterial metal being at least one metal selected from the group consisting of silver, copper and zinc, and being carded by a method including the steps of supporting at least one of a metallic salt and an ion of said antibacterial metal, on said calcium containing phosphate, and converting at least one of said metallic salt and said ion into said metallic state of said antibacterial metal.

3. A dentifrice as claimed in claim 2, wherein said calcium containing phosphate is in the form of powder.

4. A dentifrice as claimed in claim 2, wherein the step of converting includes firing said phosphate supporting at least one of said metallic salt and said ion, at a temperature not lower than 800° C.

5. A dentifrice as claimed in claim 2, wherein the step of converting includes heating said phosphate supporting at least one of said metallic salt and said ion, at a temperature not lower than 350° C. in the presence of hydrogen so as to accomplish reduction of at least one of said metallic salt and said ion.

6. A dentifrice as claimed in claim 2, wherein said calcium containing phosphate is at least one selected from the group consisting of hydroxylapatite, tricalcium phosphate and calcium diphosphate.

7. A dentifrice as claimed in claim 2, wherein said antibacterial metal is contained in an amount of not more than 30% by weight relative to said calcium containing phosphate.

8. A dentifrice as claimed in claim 7, wherein said antibacterial metal is contained in an amount ranging from 0.0001 to 5% by weight relative to said calcium containing phosphate.

9. A dentifrice comprising:

a phosphate containing calcium, said phosphate being at least one selected from the group consisting of hydroxylapatite, tricalcium phosphate, and calcium diphosphate, said phosphate being in the form of powder; and at least one antibacterial metal carried in a metallic state by said phosphate powder, said antibacterial metal being at least one selected from the group consisting of silver, copper and zinc.

10. A dentifrice comprising:

hydroxylapatite powder in the form of powder; and at least one antibacterial metal carded in a metallic state by said phosphate powder, said antibacterial metal being at least one selected from the group consisting of silver, copper and zinc.

11. A dentifrice comprising:

a phosphate containing calcium; and an antibacterial metal carried in a metallic state by said calcium containing phosphate, said antibacterial metal being at least one metal selected from the group consisting of silver, copper and zinc, and being carried by a method including the steps of adding a water-soluble salt of said antibacterial metal in water containing powder of said calcium containing phosphate so that said antibacterial metal is supported on said phosphate, separating said phosphate supporting said antibacterial metal from water, drying said separated phosphate, and converting said antibacterial metal into its metallic state so that said antibacterial metal is carried in the metallic state by said phosphate.

12. A dentifrice as claimed in claim 11, wherein the converting step includes firing said phosphate supporting said antibacterial metal, at a temperature not lower than 800° C.

13. A dentifrice as claimed in claim 11, wherein the converting step includes reducing said antibacterial metal in the presence of hydrogen.

14. A dentifrice as claimed in claim 1, wherein the dentifrice comprises tooth paste and the phosphate containing calcium and antibacterial metal carried in a metallic state by said calcium containing phosphate is selected from the group consisting of $Ca_{10-x} \cdot M_x(PO_4)_5(OH)_2$, $Ca_{10}(M \cdot PO_4)_5(OH)_2$, $Ca_{10-x} \cdot M_x(PO_4)_6(OH)_2$ and $Ca_{10}(M \cdot PO_4)_6(OH)_2$, wherein X is an integer greater than zero, and M is an antibacterial metal selected from the group consisting of silver, copper and zinc.

15. A dentifrice as claimed in claim 14, wherein said phosphate containing calcium and antibacterial metal carried in a metallic state by said calcium containing phosphate is $Ca_{10}(Ag \cdot PO_4)_6(OH)_2$.

16. A dentifrice as claimed in claim 2, wherein the dentifrice comprises tooth paste and the phosphate containing calcium and antibacterial metal carried in a metallic state by said calcium containing phosphate is selected from the group consisting of $Ca_{10-x} \cdot M_x(PO_4)_5(OH)_2$, $Ca_{10}(M \cdot PO_4)_5(OH)_2$, $Ca_{10-x} \cdot M_x(PO_4)_6(OH)_2$ and $Ca_{10}(M \cdot PO_4)_6(OH)_2$, wherein X is an integer greater than zero, and M is an antibacterial metal selected from the group consisting of silver, copper and zinc.

17. A dentifrice as claimed in claim 16, wherein said phosphate containing calcium and antibacterial metal carried in a metallic state by said calcium containing phosphate is $Ca_{10}(Ag \cdot PO_4)_6(OH)_2$.

* * * * *